United States Patent [19]

Petty

[11] Patent Number: 4,490,236

[45] Date of Patent: Dec. 25, 1984

[54] METHOD AND MEANS FOR ELECTRODE CALIBRATION

[76] Inventor: John D. Petty, 34 Palm Ave., Holland Park, Queensland, Australia

[21] Appl. No.: 489,150

[22] Filed: Apr. 27, 1983

[30] Foreign Application Priority Data

Apr. 30, 1982 [AU] Australia .............................. 83153/82

[51] Int. Cl.³ ............................................. G01N 27/28
[52] U.S. Cl. .................................. 204/409; 73/1 R; 204/416
[58] Field of Search ............... 204/400, 401, 409, 415, 204/416, 418, 419, 420, 1 T; 73/1 R, 1 G; 137/111, 114

[56] References Cited

U.S. PATENT DOCUMENTS

| | | | |
|---|---|---|---|
| 3,418,231 | 12/1968 | Haddad | 204/415 |
| 3,556,950 | 1/1971 | Dahms | 204/420 X |
| 3,997,420 | 12/1976 | Buzza | 204/420 X |

*Primary Examiner*—Howard S. Williams
*Assistant Examiner*—Nam X. Nguyen
*Attorney, Agent, or Firm*—Holman & Stern

[57] ABSTRACT

An electrode calibration apparatus which automatically calibrates a sensing electrode by providing a flow sensitive valve member which seals off flow of calibrating solution to the electrode during flow of a test solution past the electrode, but which permits calibrating solution to contact the electrode when the flow of test solution is interrupted.

22 Claims, 2 Drawing Figures

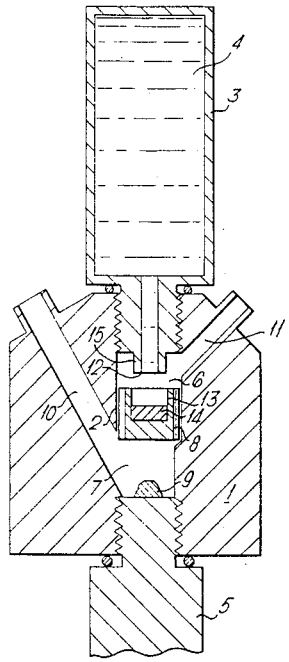

METHOD AND MEANS FOR ELECTRODE CALIBRATION

BACKGROUND OF THE INVENTION

The present invention relates generally to the electrochemical detection of substances in solution and more particularly to an improved method and means for calibrating sensing electrodes.

The measurement of substances in solution has long been determined by known techniques involving voltametric and amperemetric cells in contact with the solution to be tested. These cells act as sensing electrodes which produce voltages and currents respectively, which are proportional to the level of substance being detected. A suitable voltameter or ammeter is employed to indicate the level of substance measured.

A number of sensing electrodes are employed by those skilled in the art to measure a variety of cations, anions, dissolved gases, oxidizing and reducing substances. The well known glass pH half-cell used in conjunction with a reference half-cell, referred to herein as a combination pH electrode, which responds reversibly to the pH of a solution according to the Nernst equation, is an example. Another electrode of the general type with which this invention is concerned is the inert metal half-cell/reference half-cell, herein referred to as a combination redox electrode, which measures the oxidizing or reducing power of a solution. Yet another electrode of the general type relevant to this invention is the dissolved oxygen electrode, which produces a current in proportion to the level of dissolved oxygen in solution. Indeed, it will become apparent that the invention is not restricted to use with any particular electrode, and may be used with all types.

All of the above mentioned devices require periodic calibration to correct changes in performance or to ascertain electrode malfunction. Generally one or two solutions of known composition with respect to a given substance are employed to establish substantial compliance with the ideal cell characteristics. Calibration controls on the indicating meter are used to correct deviations.

Those acquainted with the art know that the preferred calibration solutions are those which do not change value appreciably on dilution or contamination. Such solutions are known as buffers, and the capacity of such a solution to resist effects which cause changes in value is termed buffer capacity.

It is also known in the prior art that calibration may be manual or automatic. Manual calibration necessitates the removal of the sensing electrode from the test environment and placement of the sensing electrode in the calibration solution. Automatic calibration has been accomplished by the use of a flow through cell, reservoir of calibration solution, timer and externally operated valve or valves to introduce the calibration solution.

In applications where the sensing electrode monitors a test solution flowing past the electode, certain difficulties arise with the calibration methods of the prior art. The applications of flow referred to herein and generally concerned with this invention are flows of test solution through hollow structures, generally referred to as pipes or tubes, as used in the transference of a body of solution from one space to another, or in the circulation of a fixed body of test solution. The latter application includes such as swimming pools, which employ a pump and filter to circulate the water contained in the swimming pool.

It is found that manual calibration has the disadvantage of requiring the presence of an experienced operator. In addition, removal of the sensing electrode for calibration can be hazardous if the test solution is under pressure or of a corrosive nature. It is also found that mishandling the sensing electrode results in loss of sensing ability.

A fuller understanding of the limitations of the automatic calibration method of the prior art can be gained by consideration of the following description of operation.

When the flow of test solution is stopped to allow calibration, the space surrounding the sensing tip of the electrode must be isolated from the test solution body to allow voiding and introduction of the calibration solution. This normally requires one or two externally operated valves which are capable of resisting the test solution pressure. These valves operate in conjunction with a timing device to perform calibration at prescribed intervals.

It is apparent that such devices overcome the difficulties associated with manual calibration, but are cumbersome and complicated, and are seldom used in practice.

BRIEF SUMMARY OF THE INVENTION

The present invention seeks to provide an improved method and apparatus for single solution calibration of sensing electrodes.

According to one form the present invention provides an electrode calibration apparatus comprising in combination:

a sensing electrode for measuring the quantity of a particular substance in a test solution;

a reservoir for a calibration solution;

a cell body enclosing a cavity with means to allow test solution to flow through said cavity, said sensing electrode and an outlet from said reservoir being exposed to said cavity; characterised by means for restricting access of said calibration solution from said reservoir to said sensing electrode during, and as a result of, flow of test solution through said cavity and for allowing access of said calibration solution to said tip of said sensing electrode upon termination of test solution flow.

In another form the present invention provides a method of calibrating an electrode comprising directing a test solution past said electrode and opening a closure to a source of calibrating solution which contacts said electrode when said test solution is not flowing past said electrode, the opening of said closure being dependant upon the absence of test solution flow past said electrode.

An embodiment provides an improved calibration method which eliminates the need to isolate the measurement environment from the main body of test solution. A further embodiment provides an improved calibration method which operates independently of the test solution pressure. Yet a further embodiment of the invention provides a means of automatically introducing the calibration solution to the sensing electrode immediately following cessation of the flow of test solution, without the use of an externally operated valve.

The calibration solution is chosen with the following considerations:

(a) preferably, the density of the calibration solution should not be less than that of the test solution and (b) preferably, the buffering capacity of the calibration solution should be greater than that of the test solution.

By way of example, a calibration solution consisting of 0.025M potassium dihydrogen phosphate and 0.025M disodium hydrogen phosphate, which is known to be buffered with respect to pH, and which is known to posess a density greater than that of non-salted swimming pool water, would be a suitable calibration solution for the pH calibration of a pH combination electrode used to measure the pH of non-salted swimming pool water.

Those skilled in the art, following the teachings contained herein, will recognize that many possibilities for calibration solutions exist, depending on the type of electrode employed and the nature of the test solution. Accordingly, it is intended that the abovementioned example be interpreted in an illustrative and not a limiting sense.

BRIEF DESCRIPTION OF THE DRAWING

A particular embodiment of the invention will now be described by way of example with reference to the accompanying drawings in which:

FIG. 1 is a vertical section of the electrode calibration cell assembly; and

FIG. 2 is a top plan of the valve of the cell assembly of FIG. 1.

DETAILED DESCRIPTION OF THE INVENTION

Referring to FIG. 1 which shows a cell body 1 enclosing a cell cavity 2 bounded above by a calibration solution reservoir 3 containing a quantity of calibration solution 4, and positioned above a sensing electrode 5. The cell cavity 2 comprises a valve chamber 6 and electrode chamber 7. The electrode chamber 7 is preferably smaller than moveable valve 8 so that the valve 8 cannot damage the sensing tip 9 of the electrode by resting against it. Typically body 1 is made of synthetic polymer which is substantially chemically inert to test and calibration solutions, such as acrylic plastic, polypropylene, or glass.

A sensing electrode 5 is mounted in an inverted position with its sensing tip 9 exposed to the electrode chamber 7 and sealed to the cell body 1 in a fluid tight fashion.

A passageway 10 allows test solution to enter the electrode chamber 7 and exit passageway 11 allows exit of test solution from the valve chamber 6. Both passageways 10 and 11 preferably extend upwards to minimize diffusion of calibration solution along passageways 10 and 11.

A calibration solution reservoir 3 is a closed container except for small aperture 12 exposed to valve chamber 6. Reservoir 3 is sealed to cell body 1 in a fluid tight fashion.

Moveable valve 8 has a recessed seat 13 uppermost with a cushion 14 of elastic material to form an effective seal against aperture collar 15. Typically cushion 14 is made of silicone rubber. Valve 8 is preferably grooved longitudinally to allow passage of calibration solution to the electrode chamber 7 in the no flow condition of the test solution, and passage of test solution from the inlet passageway 10 to the exit passageway 11 in the flow condition when cushion 14 seals aperture 12. Valve 8 is constructed of a suitably inert material and possesses a density greater than that of either the test or calibration solution, such as polytetra fluoroethylene.

In the flow condition of the test solution movement of the valve 8 is such as to close access of the calibration solution 4 to the cell cavity 2 and the sensing electrode measuring tip 9, and under this condition the sensing electrode measures the test solution flowing past it.

Whereas a condition of no flow of test solution allows the valve 8 to open by falling under the influence of gravity, allowing movement of the calibration solution 4 or solutes contained therein into the cell cavity 2 and around the electrode measuring tip 9 by processes of diffusion and displacement of the lighter test solution by the heavier calibration solution 4. The latter process results in the contamination of the calibration solution by the test solution, however, by virtue of the buffering capacity of the calibration solution being greater than that of the test solution, many calibrations may be performed without a need to replace the calibration solution.

Since the whole apparatus is a closed structure, its operation is found to be unaffected by variations of test solution pressure.

Since certain changes may be made in the above apparatus without departing from the scope of the invention herein involved it is intended that all matter contained in the above description or shown in the accompanying drawings shall be interpreted in an illustrative and not limiting sense.

I claim:

1. Apparatus for calibrating a tipped sensing electrode used to measure the quantity of a particular substance in a flowing test solution comprising:

a cell body enclosing a cavity having an upper portion and a lower portion;

a reservoir for a calibration solution removably positioned above said cell body;

a reservoir conduit means for flowingly connecting said reservoir to said cavity upper portion;

aperture means in said cavity lower portion adapted to removably receive the tip of said sensing electrode;

first conduit means for permitting a test solution to flowingly enter said cavity;

second conduit means for permitting said test solution to flowingly exit said cavity; and valve means entirely located within said cavity and powered solely by the flow of said test solution, for closing said reservoir conduit means when said test solution flows through said cavity and opening said reservoir conduit means when said test solution ceases flowing through said cavity; so that calibration solution may automatically be afforded to said sensing electrode tip upon termination of test solution flow.

2. The apparatus of claim 1 wherein said first conduit means enters said cavity at its lower portion and said second conduit means exits said cavity at its upper portion.

3. The apparatus of claim 2 wherein said valve means comprises a freely movable piston which is urged against said reservoir conduit means by said test solution when it is flowing thereby sealing said reservoir conduit, and drops under force of gravity when said test solution ceases flowing thereby opening said reservoir conduit.

4. The apparatus of claim 3 wherein said reservoir conduit means terminates in said cavity in an annular collar and said freely movable piston has a recessed seat in its uppermost surface adapted to form an effective seal with said annular collar when said piston is urged against said reservoir conduit means by said flowing test solution.

5. The apparatus of claim 3 wherein said reservoir is removably mounted on said cell body above said cavity.

6. The apparatus of claim 3 wherein the lower portion of said cavity is sufficiently small to prevent said valve means from contacting said sensing tip when it is inserted in said aperture.

7. The apparatus of claim 1 wherein said valve means comprises a freely movable piston which is urged against said reservoir conduit means by said test solution when it is flowing thereby sealing said reservoir conduit, and drops under force of gravity when said test solution ceases flowing thereby opening said reservoir conduit.

8. The apparatus of claim 7 wherein the lower portion of said cavity is sufficiently small to prevent said valve means from contacting said sensing tip when it is inserted in said aperture.

9. The apparatus of claim 8 wherein said reservoir conduit means terminates in said cavity in an annular collar and said freely movable piston has a recessed seat in its uppermost surface adapted to form an effective seal with said annular collar when said piston is urged against said reservoir conduit means by said flowing test solution.

10. The apparatus of claim 9 wherein said freely movable piston is longitudinally grooved, to facilitate the passage of test solution and calibration solution.

11. The apparatus of claim 10 wherein said cavity upper portion forms a cylinder operatively associated with said freely movable piston.

12. The apparatus of claim 1 wherein said reservoir is removably mounted on said cell body above said cavity.

13. The apparatus of claim 1 wherein said first conduit means and said second conduit means both extend upward.

14. The apparatus of claim 1 wherein said cell body is constructed of acrylic plastic, polypropylene or glass and said valve means is constructed of an inert material.

15. The apparatus of claim 1 in combination with a combination-pH electrode inserted in said aperture means.

16. The apparatus of claim 1 in combination with a combination-redox electrode inserted in said aperture means.

17. The apparatus of claim 1 in combination with a dissolved oxygen electrode inserted in said aperture means.

18. The apparatus of claim 1 in combination with a calibration solution in said reservoir selected from one of the group consisting of an aqueous mixture of monohydrogen phosphate and dihydrogen phosphate ions in the pH range of 6.0 to 8.0;

an aqueous solution of hypochlorite ions; or an aqueous solution of sulphite ions.

19. A method of calibrating an electrode comprising directing a test solution past said electrode, and opening a closure to a source of calibrating solution which contacts said electrode when said test solution is not flowing past said electrode, the opening of said closure being activated by the absence of test solution flow past said electrode.

20. The method as claimed in claim 19 wherein the said calibration solution is an aqueous mixture of monohydrogen phosphate and dihydrogen phosphate ions in the pH range 6.0 to 8.0.

21. A method as claimed in claim 19 wherein the calibration solution is an aqueous solution of hypochlorite ions.

22. A method as claimed in claim 19 wherein the calibration solution is an aqueous solution of sulphite ions.

* * * * *